United States Patent [19]

Seelmann-Eggebert et al.

[11] Patent Number: 4,952,655

[45] Date of Patent: Aug. 28, 1990

[54] WATER-SOLUBLE COPOLYMERS, THEIR PREPARATION AND THEIR USE

[75] Inventors: Hans-Peter Seelmann-Eggebert, Schriesheim; Dieter Boeckh; Heinrich Hartmann, both of Limburgerhof; Wolfgang Trieselt, Ludwigshafen; Alexander Kud, Eppelsheim, all of Fed. Rep. of Germany

[73] Assignee: BASF Aktiengesellschaft, Ludwigshafen, Fed. Rep. of Germany

[21] Appl. No.: 183,611

[22] Filed: Apr. 19, 1988

[30] Foreign Application Priority Data

Apr. 21, 1987 [DE] Fed. Rep. of Germany ....... 3713348

[51] Int. Cl.$^5$ .............................................. C08F 20/10
[52] U.S. Cl. ............................ 526/318.4; 526/318.41; 526/318.42; 526/318.43; 525/59
[58] Field of Search ............ 526/318.2, 318.3, 318.41, 526/318.42, 318.43, 318.4, 317.1; 525/59

[56] References Cited

U.S. PATENT DOCUMENTS 3,988,305  10/1976  Stol et al. ........................ 526/318.2
4,096,323  6/1978  Wegemund ................... 526/318.43

Primary Examiner—Joseph L. Schofer
Assistant Examiner—Alex H. Walker
Attorney, Agent, or Firm—Martin P. Connaughton; William G. Conger

[57] ABSTRACT

Water-soluble copolymers having a K value of from 15 to 120 (determined on the sodium salt according to H. Fikentscher in aqueous solution at 25° C., a pH of 7 and a polymer concentration of the Na salt of 1% by weight) contain, in the polymerized form, (a) from 99.5 to 80 mol % of one or more monoethylenically unsaturated $C_3$–$C_6$-monocarboxylic acids and (b) from 0.5 to 20 mol % of one or more comonomers which possess two or more ethylenically unsaturated, non-conjugated double bonds, are derived from esters and are obtainable by esterification of (b1) monoethylenically unsaturated $C_3$–$C_6$-monocarboxylic acids with (b2) polyhydric alcohols of 2 to 6 carbon atoms, polyalkylene glycols, polyglycerols, polyvinyl alcohol and monohydric, monoethylenically unsaturated $C_3$–$C_6$-alcohols and (c) from 0 to 30 mol % of other water-soluble, monoethylenically unsaturated monomers which are copolymerizable with (a) and (b), the copolymers containing polymer segments which consist of units of the monomers (a) and (c), have a weight average molecular weight of not more than 15,000 and are bonded to one another via units of (b).

3 Claims, No Drawings

WATER-SOLUBLE COPOLYMERS, THEIR PREPARATION AND THEIR USE

WO Application No. 85/01736 discloses seed can be coated with a polymer mixture which is hygroscopic and consists of finely divided crosslinked polyacrylamides and finely divided crosslinked polyacrylates. These mixtures may also contain graphite. The seed coated with these mixtures germinates more rapidly than untreated seed. However, the disadvantage is that the high molecular weight, crosslinked polymers are virtually completely non-biodegradable.

It is an object of the present invention to provide substantially biodegradable coating agents for seed.

We have found that this object is achieved, according to the invention, with water-soluble copolymers based on monoethylenically unsaturated carboxylic acids of 3 to 6 carbon atoms if the copolymers have a K value of from 15 to 120 (determined according to H. Fikentscher on the sodium salt in aqueous solution at 25° C., a pH of 7 and a polymer concentration of the Na salt of 1% by weight) and contain, as copolymerized units, (a) from 99.5 to 80 mol % of one or more monoethylenically unsaturated $C_3$–$C_6$-monocarboxylic acids and
(b) from 0.5 to 20 mol % of one or more comonomers which possess two or more ethylenically unsaturated, nonconjugated double bonds, are derived from esters and are obtainable by esterification of
(b1) monoethylenically unsaturated $C_3$–$C_6$-monocarboxylic acids with
(b2) polyhydric alcohols of 2 to 6 carbon atoms, water-soluble or water-insoluble polyalkylene glycols having a molecular weight of up to about 400, water-soluble polyalkylene glycols having a molecular weight from above about 400 to 10,000, polyglycerols having a molecular weight of up to 2,000, polyvinyl alcohol having a molecular weight of up to 10,000 and monohydric, monoethylenically unsaturated $C_3$–$C_6$-alcohols, and
(c) from 0 to 30 mol % of other water-soluble, monoethylenically unsaturated monomers which are copolymerizable with (a) and (b), with the proviso that the sum of the mol % data (a) to (c) is always 100 and that the polymer segments consisting of units of the monomers (a) and (c) and bonded to one another via units of (b) have a weight average molecular weight of not more than 15,000.

The water-soluble copolymers are prepared by copolymerization of a monomer mixture of (a) from 99.5 to 80 mol % of one or more monoethylenically unsaturated $C_3$–$C_6$-monocarboxylic acids and
(b) from 0.5 to 20 mol % of one or more comonomers which possess two or more ethylenically unsaturated, nonconjugated double bonds, are derived from esters and are obtainable by esterification of
(b1) monoethylenically unsaturated $C_3$–$C_6$-monocarboxylic acids with
(b2) polyhydric alcohols of 2 to 6 carbon atoms, water-soluble or water-insoluble polyalkylene glycols having a molecular weight of up to about 400, water-soluble polyalkylene glycols having a molecular weight from above about 400 to 10,000, polyglycerols having a molecular weight of up to 2,000, polyvinyl alcohol having a molecular weight of up to 10,000 and monohydric, monoethylenically unsaturated $C_3$–$C_6$-alcohols, and
(c) from 0 to 30 mol % of other, water-soluble, monoethylenically unsaturated monomers which are copolymerizable with (a) and (b), in aqueous solution in the presence of a polymerization initiator and, if necessary, a regulator, the sum of the mol % data (a) to (c) always being 100.

Suitable components (a) of the water-soluble copolymers are monoethylenically unsaturated $C_3$–$C_6$-monocarboxylic acids. Examples of suitable carboxylic acids of this type are acrylic acid, methacrylic acid, ethacrylic acid, vinylacetic acid, allylacetic acid and crotonic acid. Preferably used monomers of component (a) are acrylic acid and/ or methacrylic acid. The monomers of component (a) are present in the copolymer in an amount of up to 99.5–80, preferably 97–83, mol %.

The monomers of component (b) constitute an important component of the copolymers. These are comonomers which possess two or more ethylenically unsaturated, non-conjugated double bonds and one or more ester groups. These comonomers generally increase the molecular weight of the copolymers and are present in the latter in an amount of up to 0.5–20, preferably 3–17, mol %.

The comonomers (b) are, for example, obtainable by reacting (b1) a monoethylenically unsaturated $C_3$–$C_6$-monocarboxylic acid or a mixture thereof with
(b2) polyhydric alcohols of 2 to 6 carbon atoms, water-soluble or water-insoluble polyalkylene glycols having a molecular weight of up to about 400, water-soluble polyalkylene glycols having a molecular weight from above about 400 to 10,000, polyglycerols having a molecular weight of up to 2,000, polyvinyl alcohol having a molecular weight of up to 10,000, monohydric, monoethylenically unsaturated $C_3$–$C_6$-alcohols or a mixture of these.

Instead of the free acids, the ester-forming derivatives, such as anhydrides, acid halides or esters, in particular those with simple lower alcohols, may be used as component (b1).

Polyhydric alcohols of 2 to 6 carbon atoms are, for example, glycol, glycerol, pentaerythritol and monosaccharides, such as glucose, mannose, galactose, uronic acids, such as galacturonic acid, and sugar acids, such as mucic acid or galactonic acid.

Water-soluble polyalkylene glycols are the adducts of ethylene oxide, propylene oxide, n-butylene oxide or isobutylene oxide, or a mixture of these, with a polyhydric alcohol of 2 to 6 carbon atoms, for example the adducts of ethylene oxide with glycol, adducts of ethylene oxide with glycerol, adducts of ethylene oxide with pentaerythritol, adducts of ethylene oxide with monosaccharides and the adducts of mixtures of the stated alkylene oxides with polyhydric alcohols. These adducts may be block copolymers of ethylene oxide and propylene oxide, of ethylene oxide and butylene oxides or of ethylene oxide, propylene oxide and butylene oxides. In addition to the block copolymers, other suitable adducts are those which contain the stated alkylene oxides randomly distributed as copolymerized units. The molecular weight of the polyalkylene glycols is advantageously up to 5,000, preferably up to 2,000. Among the water-soluble polyalkylene glcyols, diethylene glycol, triethylene glycol, tetraethylene glycol and polyethylene glycol having a molecular weight of up to 1,500 are preferably used.

Other suitable components (b2) are polyglycerols having a molecular weight of up to 2,000. From this class of substances, diglycerol, triglycerol and tetraglycerol are preferably used. Polyvinyl alcohols having a molecular weight of up to 10,000, preferably up to 2,000, are also suitable. Suitable polyvinyl alcohols which are prepared from polyvinyl acetate by hydrolysis can be obtained by complete or partial hydrolysis of polyvinyl acetate.

Comonomers (b) selected from acrylic acid, methacrylic acid or methacrylic anhydride and ethylene glycol, polyethylene glycol having a molecular weight of up to 2,000, glycerol, diglycerol, triglycerol, tetraglycerol and polyglycerols having a molecular weight of up to 2,000, pentaerythritol, monosaccharides, neopentylglycol and α,ω-diols of 3 to 6 carbon atoms are preferably used.

The water-soluble copolymers are prepared by copolymerization of monomer mixtures of (a), (b) and, if required, (c) in aqueous solution in the presence of polymerization initiators and, if necessary, regulators.

The sum of the mol % data for components (a) to (c) is always 100. The copolymerization is carried out exclusively in an aqueous, preferably purely aqueous, medium. It can be carried out by various processes. For example, the monomers can be polymerized batchwise in the form of aqueous solutions by a batch procedure. It is also possible initially to take some of the monomers and some of the initiator and, where relevant, the regulator in a polymerization reactor, to heat the mixture to the polymerization temperature under an inert gas atmosphere and then to add the remaining monomers and the initiator and, where relevant, further amounts of regulator or the total amount of regulator to the reactor at the rate at which the polymerization proceeds. The polymerization temperatures are from 20° to 200° C., preferably from 40° to 150° C. At above 100° C., the reaction is carried out in a pressure apparatus.

In a preferred embodiment of the preparation process, the comonomer (b) is first prepared by a method in which (b1) methacrylic anhydride is initially taken in a reactor and reacted therein with (b2) polyhydric alcohols of 2 to 6 carbon atoms, water-soluble or water-insoluble polyalkylene glycols having a molecular weight of up to about 400, water-soluble polyhydric polyalkylene glycols having a molecular weight greater than about 400–10,000, polyglycerols having a molecular weight of up to 2,000, polyvinyl alcohol having a molecular weight of up to 10,000, monohydric, monoethylenically unsaturated $C_3$–$C_6$-alcohols or a mixture of these at from 50° to 200° C. This reaction is preferably carried out in the absence of water. Instead of the free ethylenically unsaturated carboxylic acids, or the anhydrides, the corresponding esters with monohydric $C_1$–$C_4$-alcohols can also be used as starting materials in the preparation of the comonomers (b). In these cases, a transesterification is carried out and, preferably, the resulting $C_1$–$C_4$-alcohol is distilled off from the reaction mixture. If necessary, conventional esterification catalysts may be present.

In the case of polyhydric alcohols, not less than 2 moles of a compound of component (b1) are used per mole of the compounds (b2). The temperature during the reaction is preferably from 50° to 150° C. The reaction is carried out until virtually quantitative conversion of the component (b2) is obtained. The comonomer (b) can be dissolved in a monoethylenically unsaturated $C_3$–$C_6$-monocarboxylic acid (a) and then subjected to the copolymerization together with the monomers (a) serving as solvents.

However, the comonomer (b) can also remain in the reaction mixture in which it was prepared and can be dissolved therein by the addition of water or dilute aqueous sodium hydroxide solution. This solution is then copolymerized by adding the comonomers (a) and, if necessary, (c). The copolymerization is carried out at a pH of the aqueous solution of from 2 to 9, preferably from 3 to 7. The monomers (a), each of which contain carboxyl groups, can be copolymerized in the form of the free carboxylic acids or in a neutralized, preferably partially neutralized, form, the degree of neutralization being from 0 to 100, preferably from 10 to 85, mol %. Neutralization is preferably effected using alkali metal or ammonium bases. These are, for example, sodium hydroxide solution, potassium hydroxide solution, sodium carbonate, potassium carbonate or ammonium bases such as ammonia, $C_1$–$C_{18}$-alkylamines, dialkylamines, such as dimethylamine, di-n-butylamine or dihexylamine, tertiary amines, such as trimethylamine, triethylamine, tributylamine or triethanolamine, and quaternized nitrogen bases, eg. tetramethylammonium hydroxide, trimethyllaurylammonium hydroxide and trimethylbenzylammonium hydroxide. Sodium hydroxide solution, potassium hydroxide solution or ammonia is preferably used for neutralization. However, neutralization may also be carried out using alkaline earth metal bases, for example Ca hydroxide or $MgCO_3$.

The copolymers may contain, as component (c), other, water-soluble monoethylenically unsaturated monomers which are copolymerizable with (a) and (b). Examples of suitable monomers of this type are acrylamide, methacrylamide, 2-acrylamido-2-methylpropanesulfonic acid, vinylsulfonic acid, allylsulfonic acid, vinylphosphonic acid, allylphosphonic acid, acrylonitrile, methacrylonitrile, dimethylaminoethyl acrylate, diethylaminoethyl acrylate, diethylaminoethyl methacrylate, N-vinylpyrrolidone, N-vinylformamide, N-vinylimidazole, N-vinylimidazoline, 1-vinyl-2-methyl-2-imidazoline, vinyl acetate and mixtures of the stated monomers. Those monomers of this group which contain acid groups can be used in the copolymerization in the form of the free acid groups or in a form which is partially or completely neutralized with alkali metal bases or ammonium bases. The basic acrylates, such as diethylaminoethyl acrylate, are neutralized or quaternized with acids and then subjected to the copolymerization. The monomers (c) are present in the copolymers in an amount of from 0 to 30, preferably from 0 to 20, mol %. They are used merely for modifying the copolymers.

Preferably used polymerization initiators are water-soluble free radical-forming compounds, for example hydrogen peroxide, peroxydisulfates and mixtures of hydrogen peroxide and peroxydisulfates. Examples of suitable peroxydisulfates are lithium peroxydisulate, sodium peroxydisulfate, potassium peroxydisulfate and ammonium peroxydisulfate. In the case of mixtures of hydrogen peroxide and peroxydisulfate, any ratio may be used; preferably, hydrogen peroxide and peroxydisulfate are employed in a weight ratio of from 3:1 to 1:3. Mixtures of hydrogen peroxide and sodium peroxydisulfate are preferably used in a weight ratio of 1:1. The abovementioned water-soluble polymerization initiators may furthermore be used in combination with reducing agents, for example iron(II) sulfate, sodium sulfite, sodium bisulfite, sodium dithionite, triethanolamine and ascorbic acid, in the form of redox initiators. Examples of suitable water-soluble organic peroxides are acetylacetone peroxide, methyl ethyl ketone peroxide, tert-butyl hydroperoxide and cumene hydroperoxide. The water-soluble organic peroxides too can be used with the abovementioned reducing agents. Other water-soluble polymerization initiators are azo initiators, for example 2,2'-azobis-(2-amidinopropane) dihydrochloride, 2,2'-azobis-(N,N'-dimethylene)-isobutyramidine dihydrochloride, 2-(carbamylazo)-isobutyronitrile and 4,4'-azobis-(4-cyanovaleric acid). The polymerization can also be initiated using waterinsoluble initiators, such as dibenzoyl peroxide, dicyclohexyl peroxydicarbonate, dilauryl peroxide or azoisobutyronitrile.

The initiators are used in amounts of from 0.1 to 10, preferably from 2 to 7, % by weight, based on the sum of the monomers used in the polymerization. The polymerization initiators can be added continuously or batchwise to the mixture to be polymerized, either together with the monomer or separately from this, in the form of aqueous solutions.

The copolymerization is preferably carried out in the presence of a regulator. Water-soluble compounds which are either infinitely miscible with water or soluble therein to an extent of more than 5% by weight at 20° C. are preferably used for this purpose. Compounds of this type are, for example, aldehydes of 1 to 4 carbon atoms, such as formaldehyde, acetaldehyde, propionaldehyde, n-butyraldehyde and isobutyraldehyde, formic acid, ammonium formate, hydroxylammonium salts, in particular hydroxylammonium sulfate, SH-containing compounds of not more than 6 carbon atoms, such as thioglycollic acid, mercaptoalcohols, such as mercaptoethanol, mercaptopropanol, mercaptobutanols and mercaptohexanol, monohydric and polyhydric alcohols of not more than 6 carbon atoms, such as isopropanol, glycol, glycerol and isobutanol. Preferred regulators are water-soluble mercaptans, ammonium formate and hydroxylammonium sulfate. The regulators are used in amounts of from 0 to 25% by weight, based on the sum of the monomers used in the polymerization. The particularly effective regulators, which are preferred, are employed in amounts of from 2 to not more than 15% by weight. If the reaction is carried out in the presence of a regulator, the minimum amount used is 0.2% by weight, based on the monomers to be polymerized.

Copolymers are particularly preferably prepared from
(a) acrylic acid and/or methacrylic acid and
(b) diacrylates and/or dimethacrylates of ethylene glycol, neopentylglycol, glycerol, polyethylene glycol having a molecular weight of up to 1,500 and butane-1,4-diol.

The copolymerization of the monomers (a) and (b) gives aqueous polymer solutions which have a polymer content of up to 70% by weight. It is of course also possible to prepare very dilute, for example 1% strength, aqueous solutions, but for economic reasons the copolymerization is carried out in such a way that not less than 20% strength by weight aqueous copolymer solutions are prepared. After the copolymerization, the solutions may be brought to a pH of from 6.5 to 7, unless the polymerization has in any case been carried out in this range. The copolymers can be obtained by evaporating down the aqueous solutions. They have a low residual monomer content and are, surprisingly, biodegradable. The biodegradability of the novel copolymers is up to 100% according to DIN 38,412, Part 24, Static Test (L25) and is as a rule from 20 to 95%. The K value of the copolymers (determined according to H. Fikentscher) is preferably from 20 to 80.

The copolymers are water-soluble. If they do not dissolve in water when in the free acid form, they can be converted into a water-soluble form by partial or complete neutralization with NaOH, KOH, ammonia or an amine. Copolymers and their alkali metal or ammonium salts which have a solubility of not less than 20 g per litre of water at 20° C. are regarded as water-soluble in the present context. The copolymers surprisingly have the advantage that they are not precipitated at low polymer concentrations in aqueous solutions containing Ca and/or Mg ions. It is therefore possible to prepare stable solutions of the copolymers in tap water without the alkaline earth metal salts of the copolymers being precipitated.

The copolymers contain polymer segments of units of the monomers (a) and, if desired, (c), having a weight average molecular weight of up to 15,000, preferably from 300 to 8,000. These polymer segments can be detected analytically, for example by subjecting the copolymers to hydrolysis for from 4 to 6 hours at an alkaline pH, for example at pH 9–14, and at up to 100° C. in an aqueous medium. After the hydrolysis, the reaction products are precipitated from the aqueous solution by adding organic, water-miscible solvents, such as methanol, acetone, isopropanol or a mixture of methanol and acetone. The precipitated product is washed with a solvent (methanol or acetone) and then dried. The molecular weights of the hydrolysis products are determined by gel permeation chromatography (GPC) using aqueous eluants. Calibration of the separating columns is effected by means of polystyrenesulfonates having a narrow distribution, from Pressure Chem. Comp., and conversion to the molecular weight units of Na polyacrylate according to the universal calibration principle of BENOIT (J. Chim. Phys. 63 (1969), 1507), using the measured data of Spatorico and Beyer, J. Appl. Polym. Sci. 19 (1975), 2933).

The copolymers are used as coating agents for seed. With the aid of the seed coating, all types of cereals, such as wheat, rye, oats and barley, as well as corn and lupins and other seed can be coated with a polymer film, and more rapid germination of the seed compared with the uncoated seed is achieved after sowing. From 0.1 to 1, preferably from 0.15 to 0.25, kg of copolymer is used per 100 kg of seed. The copolymers are preferably sprayed in the form of a dilute aqueous solution onto the seed, where they form a protective polymer film. Finely divided, inert fillers, for example graphite, quartz, talc or bentonite, having a particle size of from 20 to 500 pm can be incorporated in the polymer film. The fillers are preferably applied together with the polymer solution to the material to be coated.

The K values stated in the Examples were determined according to H. Fikentscher, Cellulosechemie, 13 (1932), 58–64 and 71–74; $K = k \times 10^3$. The measurements were carried out on the sodium salt in aqueous solution at 25° C., a pH of 7 and a polymer concentration of the Na salt of 1% by weight. Where novel copolymers are obtained in the form of other salts or the free acids, they first have to be converted into the sodium salts before the K value is determined. The molecular weights stated in the Examples are the number average molecular weights. The data on biodegradability were determined according to DIN 38,412, Part 24, Static Test (L25).

EXAMPLES

General Preparation Method I 300 ml of fully demineralised water are initially taken at from 95° to 100° C. in a 2 l glass reactor provided with a stirrer, thermometer, three feed vessels and an inert gas feed line, and, beginning at the same time, from 0.02 to 0.08 mole of monomer (b), dissolved in 1.38 moles of monomer (a) and 10 parts by weight of regulator in 50 ml of water are metered in over a period of 4 h and 2 parts by weight of sodium peroxodisulfate, dissolved in 50 ml of water, are metered in over a period of 4.5 h. Thereafter, the reaction mixture is cooled to 80° C., 0.2 part by weight of 2,2'-azobis-(2-amidinopropane) dihydrochloride is added and polymerization is continued for 1 h. After cooling, neutralization is carried out with 50% strength sodium hydroxide solution until a pH of 6.5 is reached.

General Preparation Method II 100 ml of fully demineralised water are initially taken at 80° C. in a 2 l glass reactor provided with a stirrer, thermometer, three feed vessels and an inert gas feed line, and, beginning at the same time, a solution of 1.38 moles of the sodium salt of monomer (a) in 200 ml of fully demineralised water and from 0.02 to 0.08 mole of monomer (b) dissolved in from 6 to 10 parts by weight of regulator are metered in over a period of 4 h and 2 parts by weight of 2,2'-azobis-(2-amidinopropane) dihydrochloride in 50 ml of water are metered in over a period of 5 h. Thereafter, polymerization is continued for a further 2 h at 80° C. After cooling, neutralization is carried out with 50% strength sodium hydroxide solution until a pH of 6.5 is reached.

General Preparation Method III 100 ml of fully demineralised water are initially taken at 80° C. in a 2 l glass reactor provided with a stirrer, thermometer, 4 feed vessels and an inert gas feed line, and, beginning at the same time, a solution of from 0.03 to 0.08 mole of monomer (b) in 1.38 moles of monomer or monomer mixture (a), from 6 to 10 parts by weight of regulator, dissolved in 50 ml of water, and from 0.69 to 1.38 moles of sodium hydroxide, as a 25% strength solution in water, are metered in over a period of 4 h and 2 parts by weight of 2,2'-azobis-(2-amidinopropane) dihydrochloride, dissolved in 50 ml of water, are metered in over a period of 5 h. Thereafter, polymerization is continued for a further 2 h at 80° C. and the pH is brought to 6.5 with 50% strength NaOH.

TABLE 1

Examples according to method I

| Example No. | Monomer (a) [mol %] | Monomer (b) [mol %] | Regulator [% by wt.] | K value | Biodegradation [%] |
|---|---|---|---|---|---|
| 1 | AS 97.1 | PEG$_{400}$ diacrylate[(1)] 2.9 | ME 10 | 28.2 | 89 |
| 2 | AS 95.8 | ethylene glycol diacrylate 4.2 | ME 10 | 38.7 | 68 |
| 3 | AS 94.7 | butanediol dimethacrylate 5.3 | TGS 10 | 31.0 | 61 |
| 4 | AS 94.7 | tripropylene oxide diacrylate 5.3 | TGS 10 | 25.4 | 52 |
| 5 | AS 98.5 | PEG$_{1500}$ diacrylate 1.5 | TGS 10 | 47.2 | 91 |
| 6 | AS 94.7 | neopentylglycol diacrylate 5.3 | TGS 10 | 28.7 | 67 |

TABLE 2

Examples according to method II

| Example No. | Monomer (a) [mol %] | Monomer (b) [mol %] | Regulator [% by wt.] | K value | Biodegradation [%] |
|---|---|---|---|---|---|
| 7 | AS 95.8 | PEG$_{1500}$ diacrylate 4.2 | ME 6 | 20.9 | 94 |
| 8 | AS 97.9 | PEG$_{1500}$ diacrylate 2.1 | BA 10 | 65.0 | 63 |
| 9 | AS 94.7 | tetraethylene oxide dimethacrylate 5.3 | ME 10 | 28.1 | 53 |
| 10 | AS 95.8 | ethylene glycol diacrylate 4.2 | ME 10 | 23.1 | 66 |
| 11 | AS 95.8 | tripropylene oxide diacrylate 4.2 | ME 10 | 37.1 | 52 |

Abbreviations:
PEG$_{400}$ = polyethylene glycol having a molecular weight of 400
PEG$_{400}$ diacrylate = diacrylate of polyethylene glycol having a molecular weight of 400
AS = acrylic acid
MAS = methacrylic acid
ME = mercaptoethanol
TGS = thioglycollic acid
BA = butyraldehyde
AF = ammonium formate

TABLE 3
Examples according to method III

| Example No. | Monomer (a) [mol %] | Monomer (b) [mol %] | Regulator [% by wt.] | K value | Residual content Monomer (a) [%] | Bidegradation [%] |
|---|---|---|---|---|---|---|
| 12 | AS 95.8 | PEG$_{1500}$ diacrylate 4.2 | ME 6 | 31.8 | 0.23 | 93 |
| 13 | AS 95.8 | ethylene glycol acrylate 4.2 | ME 10 | 22.4 | 0.37 | 69 |
| 14 | AS 96.9 | PEG$_{400}$ diacrylate 3.1 | ME 10 | 44.7 | 0.22 | 72 |
| 15 | A 85.8/10.5 | triethylene oxide diacrylate 3.7 | ME 10 | 31.5 | 0.31 | 61 |
| 16 | AS 94.7 | ethylene glycol acrylate 5.3 | AF 10 | 41.9 | 0.27 | 67 |
| 17 | AS 94.4 | pentaerythritol triacrylate 5.6 | AF 10 | 22.0 | 0.29 | 70 |
| 18 | AS 94.7 | butane-1,4-diol dimethylacrylate 5.3 | AF 10 | 22.4 | 0.25 | 54 |
| 19 | AS 94.7 | thiodiethylene glycol diacrylate 5.3 | AF 10 | 25.7 | 0.26 | 68 |
| 20 | AS 95.8 | tripropylene oxide diacrylate 4.2 | ME 10 | 55.4 | 0.41 | 47 |

The biodegradability of copolymers was additionally demonstrated by experiments on bacteria growth. For this purpose, a concentrating medium was prepared on solid nutrient substrates and solidified with 18 g/l of agar. The concentrating medium had the following composition:

| | |
|---|---|
| disodium hydrogen phosphate dihydrate | 7 g/l |
| potassium dihydrogen phosphate | 3 g/l |
| sodium chloride | 0.5 g/l |
| ammonium chloride | 1.0 g/l |
| solution of trace elements | 2.5 ml/l pH 7.0 |

(prepared according to T. Bauchop and S. R. Elsden, J. gen. Mikrobiol. 23 (1960), 457–469).

The copolymers described in Table 1 under nos. 1, 2 and 5 were each added to the nutrient media in concentrations of 10 g/l.

Soil samples were either introduced into a liquid medium and shaken there for 7 days at 30° C. or transferred directly to solid nutrient substrates as an aqueous suspension and likewise incubated at 30° C. The concentrating cultures in the liquid medium were transferred to solid nutrient substrates after 7 days. From these plates, colonies exhibiting good growth were removed and were checked for uniformity by smearing thinly.

Bacteria cultures which clearly showed growth on the copolymers investigated were isolated in this manner.

If, on the other hand, the bacterial growth experiments described above were carried out, for comparison, with a copolymer of 30% by weight of maleic acid and 70% by weight of acrylic acid, having a K value of 60, no bacterial growth could be detected.

For the copolymers stated under nos. 1, 2 and 5 in Table 1, the precipitation behavior was tested at pH 7.5 in aqueous solutions which contained from 10 to 10,000 mg/l of Ca ions (in the form of CaCl$_2$). The following Ca ion concentrations were used: 10, 50, 75, 100, 150, 500, 1,000 and 10,000 mg/l. The copolymer concentrations were varied from 0.1 to 7 mg/l (the following concentrations were tested: 0.1, 0.5, 1.0, 2, 3, 4 and 7 mg of copolymer per l of water). Even after storage of the aqueous solutions of the copolymers for 20 days in the presence of Ca ions, no precipitation occurred, whereas a copolymer of 30% by weight of maleic acid and 70% by weight of acrylic acid, having a K value of 60, was always precipitated under the stated conditions.

General Preparation Method IV 150 ml of water are initially taken in a 2 l glass reactor equipped with a stirrer, a thermometer, a condenser, a nitrogen feed line and 3 feed vessels, one of these feed vessels being heatable and stirrable, and are heated to 80° C. while flushing with nitrogen. At the same time, 0.125 mole (19.25 g) of methyacrylic anhydride and 0.0626 mole of the diols stated in Table 4 are stirred in the heatable feed vessel at 100° C. with the addition of 0.1 g of p-toluenesulfonic acid until esterification is complete (duration about 2 hours), the mixture is cooled to 30° C. and 2.875 mole (247 g) of methacrylic acid and 320 g of 25% strength aqueous sodium hydroxide solution are then added.

For polymerization, the solution prepared above and the amounts of regulator stated in Table 4 (these are based on the total amount of monomer in % by weight), dissolved in 150 ml of water, are then added over a period of 4 hours and, beginning at the same time, the amounts of initiator likewise stated in the Table, based on the total weight of the monomers, and dissolved in 150 ml of water are added over a period of 5 hours. The viscous solution is polymerized for a further hour at 90° C. after the addition of the initiator is complete. The solution is cooled to 25° C. and then brought to pH 6.5 with 25% strength aqueous sodium hyroxide solution. Table 4 summarizes the experimental results.

TABLE 4
Examples according to method IV

| Example No. | Diol | Crosslinking agent [mol %] | MAS [mol %] | Regulator [% by wt.] | Initiator [% by wt.] | K value | Residual monomer content % | Biological degradation [%] |
|---|---|---|---|---|---|---|---|---|
| 21 | ethylene glycol | 2 | 98 | 5-hydroxylammonium sulfate | 5 H$_2$O$_2$ | 30.2 | 0.21 | 66 |
| 22 | neopentylglycol | 2 | 98 | 5-hydroxylammonium sulfate | 5 H$_2$O$_2$ | 33.7 | 0.19 | 69 |

TABLE 4-continued

Examples according to method IV

| Example No. | Diol | Crosslinking agent [mol %] | MAS [mol %] | Regulator [% by wt.] | Initiator [% by wt.] | K value | Residual monomer content % | Biological degradation [%] |
|---|---|---|---|---|---|---|---|---|
| 23 | PEG$_{400}$ | 2 | 98 | | 5 H$_2$O$_2$ | 46.3 | 0.23 | 74 |
| 24 | diethylene glycol | 2 | 98 | | 2.5 H$_2$O$_2$ | 50.2 | 0.28 | 71 |
| 25 | ethylene glycol | 2 | 98 | 2,5-hydroxylammonium sulfate | 2.5 H$_2$O$_2$ | 44.3 | 0.21 | 53 |
| 26 | neopentylglycol | 2 | 98 | 2,5-hydroxylammonium sulfate | 2.5 H$_2$O$_2$ | 50.1 | 0.17 | 57 |
| 27 | diethylene glycol | 2 | 98 | 2,5-mercaptoethanol | 2.5 H$_2$O$_2$ | 42.3 | 0.13 | 63 |
| 28 | PEG$_{400}$ | 2 | 98 | | 2.5 H$_2$O$_2$ | 54.3 | 0.26 | 67 |

We claim:

1. A water-soluble copolymer based on monoethylenically unsaturated carboxylic acids of 3 to 6 carbon atoms, wherein the copolymer has a K value of from 15 to 120 (determined on the sodium salt according to H. Fikentscher in aqueous solution at 25° C., a pH of 7 and a polymer concentration of the Na salt of 1% by weight) and contains, as copolymerized units, (a) from 99.5 to 80 mol % of one or more monoethylenically unsaturated C$_3$–C$_6$-monocarboxylic acids and (b) from 0.5 to 20 mol % of one or more comonomers which possess two or more ethylenically unsaturated, nonconjugated double bonds, are derived from esters and are obtainable by esterification of (b1) monoethylenically unsaturated C$_3$–C$_6$-monocarboxylic acids with (b2) polyhydric alcohols of 2 to 6 carbon atoms, water-soluble or water-insoluble polyalkylene glycols having a molecular weight up to about 400, water-soluble polyalkylene glycols having a molecular weight from above about 400 to 10,000, polyglycerols having a molecular weight of up to 2,000, polyvinyl alcohol having a molecular weight of up to 10,000 and monohydric, monoethylenically unsaturated C$_3$–C$_6$-alcohols and (c) from 0 to 30 mol % of other water-soluble, monoethylenically unsaturated monomers which are copolymerizable with (a) and (b), with the proviso that the sum of the mol % data (a) to (c) is always 100 and the polymer segments consisting of units of monomers (a) and (c) and bonded to one another via units of (b) are polymer segments having a weight average molecular weight of not more than 15,000.

2. A water-soluble copolymer as claimed in claim 1, wherein the copolymerized comonomer (b) is obtainable by reacting (b1) acrylic acid, methacrylic acid, crotonic acid, vinylacetic acid, methacrylic anhydride or a mixture of these with (b2) polyhydric alcohols of 2 to 6 carbon atoms, water-soluble or water-insoluble polyalkylene glycols having a molecular weight of up to about 400, water-soluble polyalkylene glycols having a molecular weight from above about 400 to 10,000, polyglycerols having a molecular weight of up to 2,000, polyvinyl alcohol having a molecular weight of up to 10,000, allyl alcohol or a mixture of these.

3. A water-soluble copolymer as claimed in claim 1, wherein the polymer segments consisting of units of the monomers (a) and bonded via units of (b) are polymer segments having a weight average molecular weight of from 300 to 8,000.

* * * * *